United States Patent [19]

Eventoff

[11] Patent Number: 5,052,119

[45] Date of Patent: Oct. 1, 1991

[54] ANGULAR MICRO-POSITIONING DEVICE

[75] Inventor: Arnold T. Eventoff, Pleansantville, N.Y.

[73] Assignee: North American Philips Corp., New York, N.Y.

[21] Appl. No.: 660,242

[22] Filed: Feb. 21, 1991

Related U.S. Application Data

[63] Continuation of Ser. No. 457,436, Dec. 27, 1989, abandoned.

[51] Int. Cl.[5] .............................................. G01B 5/00
[52] U.S. Cl. ..................................... 33/569; 33/1 N; 33/1 PT; 33/573
[58] Field of Search ................. 33/569, 570, 573, 613, 33/1 N, 1 PT

[56] References Cited

U.S. PATENT DOCUMENTS

| | | | |
|---|---|---|---|
| 3,270,423 | 9/1966 | Birrell et al. | 33/569 |
| 3,810,312 | 5/1974 | Carson | 33/1 N |
| 3,876,301 | 4/1975 | Kosugi et al. | 33/1 PT |
| 3,924,338 | 12/1975 | Kindl | 33/569 |
| 3,967,178 | 6/1976 | Morris . | |
| 4,033,541 | 7/1977 | Malueg . | |
| 4,071,760 | 1/1978 | Lemay . | |
| 4,074,579 | 2/1978 | Franzolini . | |
| 4,135,305 | 1/1979 | Krause | 33/570 |
| 4,357,841 | 11/1982 | Mote . | |
| 4,362,977 | 12/1982 | Evans . | |
| 4,456,193 | 6/1984 | Westover . | |
| 4,654,571 | 3/1987 | Hinds . | |
| 4,757,818 | 7/1988 | Angelsen . | |

Primary Examiner—Harry N. Haroian
Attorney, Agent, or Firm—William L. Botjer

[57] ABSTRACT

An angular micro-positioning system cable of readily accessing any angle within 360° and thereafter precisely addressing an angular position within one ten-thousandth of a degree. The device is suitable for use in test equipment or any equipment requiring extremely precise angular positioning. The device includes a rotary motor which is mounted to a secondary frame which is pivotally mounted to a flexibly mounted main frame. The drive shaft of the rotary motor is biased in to engagement with the output wheel. A linear micro-positioner is mounted to the main frame and its drive shaft is coupled to the rotary motor frame to pivot same. The rotary motor is first rotated with the linear micro-positioner locked in place to provide coarse angle positioning. Thereafter, the drive shaft of the rotary motor is locked and the motor frame is pivoted by the linear micro-positioner which provides extremely fine angular adjustment.

5 Claims, 1 Drawing Sheet

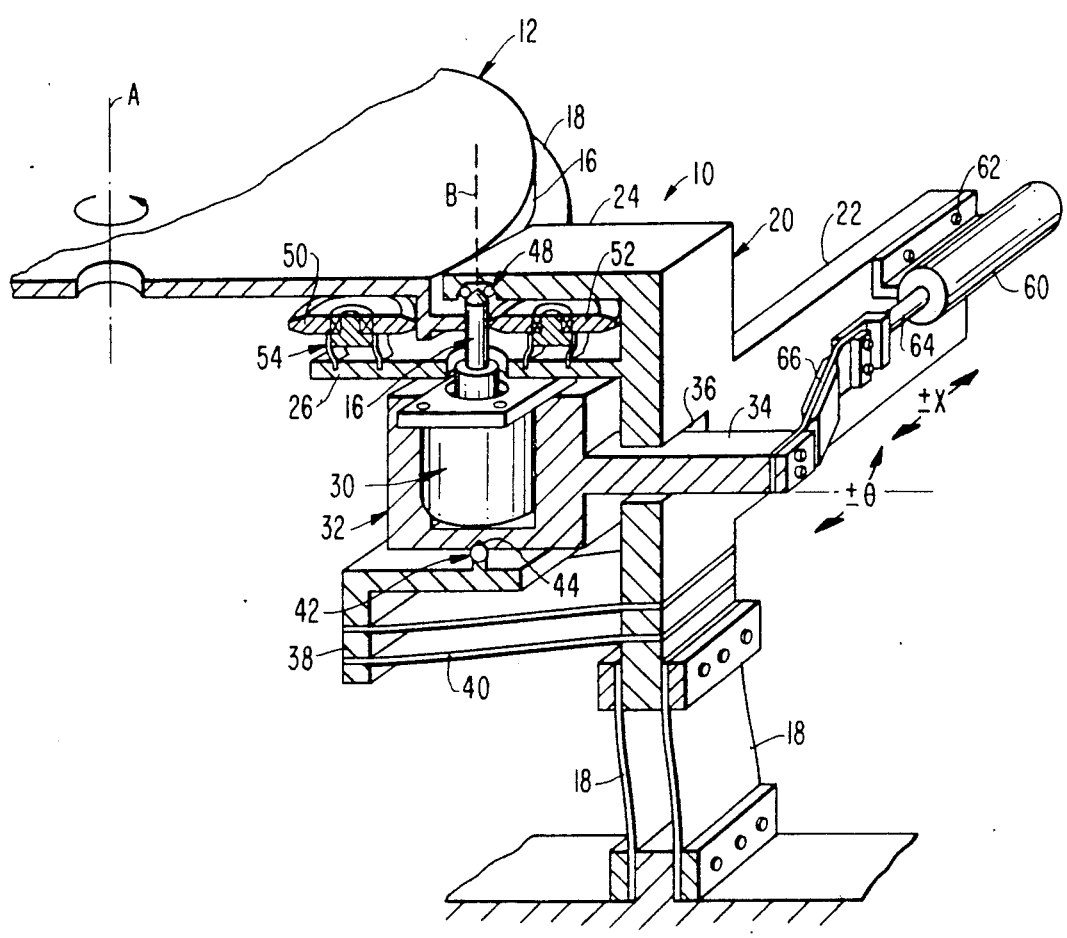

ANGULAR MICRO-POSITIONING DEVICE

This is a continuation of application Ser. No. 07/457,436 filed Dec. 27, 1989, now abandoned.

BACKGROUND OF THE INVENTION

This invention relates to a device for precisely angularly positioning a rotating device. Specifically, this invention is directed to a device capable of rapidly accessing any angle within 360° and thereafter precisely addressing a extremely fine angle.

Many devices, particularly measuring devices require that an output wheel be precisely angularly positioned. For example, X-ray diffractometers require that the sample to be measured be rotated with extremely fine resolution. However, the devices used to provide such resolution have been less than completely satisfactory. Such angular output positioning devices have often times utilized finely toothed gears. However, no matter how finely toothed the gearing, a gear drive suffers from two positioning problems. These problems are known as backlash and coasting. Backlash refers to the problem that before a gear is driven by a driving gear, the driving gear must take up slack before the driven gear moves. Coasting refers to the fact that the driven gear may keep moving after the driving gear stops. Belt drive arrangements are too flexible and subject to vibration. These factors can create accuracy errors when rotational resolution as fine as an arc-second or less is required.

Another problem with devices used for fine angular micro-positioning is that while a device may be capable of fine micro-positioning, it may not be capable of rotating the output device through a full 360°. Often a second, coarse drive mechanism is necessary. Clearly, a device capable of driving an output wheel through a full 360° and thereafter micro-positioning same, is desirable. The present invention is directed to providing such a device.

SUMMARY OF THE INVENTION

An angular micro-positioning system capable of radily accessing any angle within 360° and thereafter precisely addressing an angular position within one millionth of a degree. The device is suitable for use in test equipment or any equipment requiring extremely precise angular positioning. The device includes a rotary motor which is mounted to a secondary frame which is pivotally mounted to a main frame which in turn is flexibly mounted with respect to the output wheel. The drive shaft of the rotary motor is biased into engagement with the output wheel. A linear micro-positioner is mounted to the fixed frame and its drive shaft is coupled to the rotary motor frame to pivot same. The rotary motor is 1 first rotated with the linear micro-positioner locked in place to provide coarse angle positioning. Thereafter, the drive shaft of the rotary motor is locked and the motor frame is pivoted by the linear micro-positioner which provides extremely fine angular adjustment. The present device eliminates both backlash and coasting.

BRIEF DESCRIPTION OF THE DRAWING

For a better understanding of the invention, reference is made to the following drawing, to be taken in conjunction with the detailed specification to follow:

The drawing Figure is a perspective view, in partial cross-section, of the angular micro-positioning device constructed in accordance with the invention.

DESCRIPTION OF THE PREFERRED EMBODIMENTS

The drawing Figure illustrates the angular micro-positioning device 10 which is utilized to rotate and micro-position an output traction wheel 12 which is rotatable about an axis A. Output traction wheel 12 includes a depending flange 16 and protruding rim 18 the edge of which, as will be described in detail below, engages the drive shaft of a rotary motor. The components of the angular micro-positioning system 10 are mounted to a flexibly supported main frame 20 which includes a rearwardly extending arm 22 and inwardly extending arms 24 and 26. Main frame 20 is flexibly supported off the ground by means of flexures 18 which are arranged to permit frame 20 to be displaced radially with respect to output wheel 12 but are rigid in a circumferential direction.

Coarse positioning of output wheel 12 is accomplished by a rotary motor 30 (which may be a stepping motor) which is fixedly mounted to pivotable motor housing 32 which includes a moment arm 34 which extends through a notch 36 in main frame 20. Motor housing 32 is pivotally mounted to main frame 20 so that motor 30 is pivotatable about the longitudinal axis of its drive shaft 46, shown as axis B in the draWing Figure. The pivotal mounting of motor housing 32 is accomplished by a floating frame 38 which is coupled to main frame 20 through cantilever leaf springs 40 which serve to urge floating frame 38 towards motor housing 32. A ball bearing 42 is disposed between floating frame 38 and a notch 44 in the lower portion of motor housing 32 to permit motor housing 32 to pivot with respect to frame 38. Extending upwardly from rotary motor 30 is drive shaft 46, the upper portion of which extends into a conical ball bearing 48 disposed in inwardly extending arm 24 of main frame 20. A pair of pinch rollers 50, 52 are mounted to inwardly extending arm 26 of main frame 20 by means of flexure springs 54 which serve to urge drive shaft 46 into contact with rim 18 of traction drive wheel 12 to drive same in a capstan like arrangement.

A linear micro-positioner 60 is mounted by mean of a bracket 62 to rearwardly extending arm 22 of main frame 20. Linear micro-positioner 60 has an output shaft 64 which is coupled to moment arm 34 of motor housing 32 by means of a dual cantilever spring coupling 66 which serves as a play free link TM between output shaft 64 and motor housing 32 to permit pivoting of motor housing 32 and thus motor 30 upon activation of linear micro-positioner 60.

Both the rotary and linear drive mechanisms are used to obtain the desired angular position of output wheel 12. By way of example, rotary motor 30 coupled to the traction drive shaft 26 first drives the output traction wheel 12 to access any angle within 0.003 degrees. Then, linear micro-positioner 60 (in this case, an "Inchworm" from Burleigh Instruments, Inc.), coupled to moment arm 34 on the motor housing 32, positions output traction wheel 12 to within $1 \times -10^{-6}$ degrees.

As noted above, stepping motor housing 32 (fixed to motor 30) is pivotable about axis B coincident with the centerline of the motor armature. Lower motor housing pivot 42 and upper bearing and motor housing pivot 48 support this angular displacement of $+/-\theta$ (where θ=7.2 degrees in the device). To eliminate radial play from these pivots, springs 40 provide the required bearing axial preload. Dual cantilever spring coupling 66 converts the linear motion of the linear micro-positioner 60 to rotary motion to proportionally within a small fraction of a percent throughout its entire stroke.

During operation, while rotary motor 30 is rotating or stepping, the linear micro-positioner 60 is held stationary (electrically). While the linear micro-positioner 60 is operating, motor shaft 46 is magnetically locked to motor housing 32 and to moment arm 34, causing these elements to behave as an extremely stiff link. As a consequence, relatively large excursions of linear micro-positioner 60 result in very small rotations of the output traction wheel 12. In a model that was constructed, the ratio of the output wheel diameter to that of the drive shaft is 114, and the ratio of the moment arm radius to that of the traction drive shaft is approximately 80. With an output wheel diameter of approximately 30 cm. and a movement arm 34 of 4 inches, a 1.0 micron excursion of the micro-positioner results in a 0.000005 degree angular displacement of output wheel 12 with no measurable backlash or hysteresis. However, linear micro-positioners such as described above are capable of linear excursions of only one-tenth micron which will result in a 0.0000005 angular displacement of output wheel 12.

Accordingly, it is seen that angular micro-positioning device 10 constructed in accordance with the present invention is capable of driving output wheel 12 through a full 360° rotation while providing extremely fine angular micro-positioning. It is however to be understood that modifications and variations in the apparatus and methodology of use of the device may be resorted to without departing from the basic concept of the invention. Such modifications are deemed to be within the purview and scope of the invention and the appended claims.

What is claimed is:

1. An angular micro-positioning device for driving a rotating output device comprising:

a frame, said frame being disposed proximate to said rotating output device;

a rotary motor, said rotary motor having a drive shaft in engagement with said rotating output device for rotating same;

means for mounting said rotary motor, said motor mounting means being pivotally mounted to said frame for pivoting said motor along the longitudinal axis of its drive shaft;

linear motion driver means, mounted to said frame and having an output shaft connected to said rotary motor mounting means for pivoting said motor mounting means upon activation of said linear motion driver means;

means for locking said rotary motor against rotation of its drive shaft;

means for locking said linear motion driver means against movement of its output shaft; and control means for locking said linear motion driver means and activating said rotary motor to output relatively large rotational movements to said output device and thereafter locking the drive shaft of said rotary motor and activating said linear motion driver means to pivot said rotary mounting means and thereby pivot said rotary motor to permit fine adjustment of the angular position of said rotating output device.

2. The angular positioning system as claimed in claim 1 further including means for biasing said drive shaft of said rotary motor into engagement with said rotary output device.

3. The angular positioning system as claimed in claim 2 wherein said means for biasing said drive shaft of said rotary motor into engagement with said rotating output device comprise first and second pinch rollers mounted for rotation to said frame, one of said pinch rollers engaging said rotating output device and the other of said pinch rollers engaging said drive shaft of said rotary motor.

4. The angular micro-positioning system as claimed in claim 1 wherein said linear motion drive means is connected to said motor mounting means by a cantilever leaf spring to provide play free coupling therebetween.

5. The angular positioning system as claimed in claim 1 wherein said motor mounting means are pivotally mounted to said frame means by at least one pre-load spring for biasing said motor mounting means upwardly.

* * * * *